US006841166B1

(12) United States Patent
Zhang et al.

(10) Patent No.: US 6,841,166 B1
(45) Date of Patent: Jan. 11, 2005

(54) NITRIC OXIDE-RELEASING POLYMERS INCORPORATING DIAZENIUMDIOLATED SILANE DERIVATIVES

(75) Inventors: Huiping Zhang, Mount Vernon, IN (US); Mark E. Meyerhoff, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/226,094

(22) Filed: Aug. 21, 2002

Related U.S. Application Data

(60) Provisional application No. 60/314,177, filed on Aug. 21, 2001.

(51) Int. Cl.$^7$ ............................. A61K 9/00; A61F 13/00
(52) U.S. Cl. ...................... 424/443; 424/78.27; 424/718
(58) Field of Search ................................ 424/400, 443, 424/180.1, 181.1, 78.27, 718, 78.08

(56) References Cited

U.S. PATENT DOCUMENTS

| | | | |
|---|---|---|---|
| 5,185,376 A | | 2/1993 | Diodati et al. ............... 514/611 |
| 5,994,444 A | | 11/1999 | Trescony et al. ............. 524/429 |
| 6,200,558 B1 | * | 3/2001 | Saavedra et al. .......... 427/78.08 |
| 6,270,779 B1 | * | 8/2001 | Fitzhugh et al. ............. 424/400 |
| 6,379,660 B1 | * | 4/2002 | Saavedra et al. .......... 424/78.08 |
| 6,379,691 B1 | * | 4/2002 | Tedeschi et al. ............. 424/423 |
| 6,403,759 B2 | * | 6/2002 | Stamler et al. .............. 528/373 |
| 6,410,622 B1 | * | 6/2002 | Endres ......................... 524/189 |

OTHER PUBLICATIONS

H. Zhang et al., "Nitric Oxide–Releasing Fumed Silica Particles: Synthesis, Characterization, and Biomedical Applications", J. Am. Chem. Soc., 125, 5015–5024 (2003).*
Keefer, "Biomaterials: Thwarting Thrombus", Nature Materials 2, 357–358 (2003).*
Espades–Torre, et al., Thromboresistant Chemical Sensors Using Combined Nitric Oxide Release/Ion Sensing Polymeric Films, *J. Am. Chem. Soc.*, vol. 119, pp. 2321–2322 (1997).
Mowery, et al., More Biocompatible Electrochemical Sensors Using Nitric Oxide Release Polymers, *Electroanalysis*, vol. 11, No. 10–11, pp. 681–686 (1999).
Mowery, et al., Preparation and Characterization of Hydrophobic Polymeric Films that are Thromboresistant via Nitric Oxide Release, Biomaterials, Vol. 21, pages 9–21 (2000).
Schoenfisch, et al., Improving the Thromboresistivity of Chemical Sensors via Nitric oxide Release: Fabrication and in vivo Evaluation of NO–Releasing Oxygen–Sensing Catheters, *Anal Chem.*, vol. 72, No. 6, pp. 1119–1126 (Mar. 15, 2000).
Smith, et al., Nitric Oxide–Releasing Polymers Containing the [N(O)NO] Group, *J. Med. Chem.*, vol. 38, pp. 1148–1156 (1996).
Zhang, et al., Synthesis of Nitric Oxide Releasing Rubbers for Biomedical Applications, Abstract for American Chemical Society Meeting (Aug. 21, 1999).
Zhang, et al., More Blood Compatible Silicone Rubbers via Nitric Oxide Release, Abstract for Biomaterials Meeting (May 2000).

* cited by examiner

*Primary Examiner*—H. Thi Le
(74) *Attorney, Agent, or Firm*—Dieker & Associates, P.C.

(57) ABSTRACT

Biocompatible polymeric materials capable of providing in situ release of nitric oxide (NO) included diazeniumdiolated fumed silica as a filler in a multilayer polymer structure to release NO upon contact with water (blood). The blood-contacting polymer surface is preferably multi-layered so that the NO-releasing layer, containing the diazeniumdiolated fumed silica, is shielded from blood contact by one or more top (or base) coats. When in contact with blood, the NO released at the surface of the polymer prevents platelet activation and adhesion to the surface, thereby reducing platelet consumption, risk of thrombus formation and other clinical complications associated with interactions between blood and foreign materials.

11 Claims, 6 Drawing Sheets

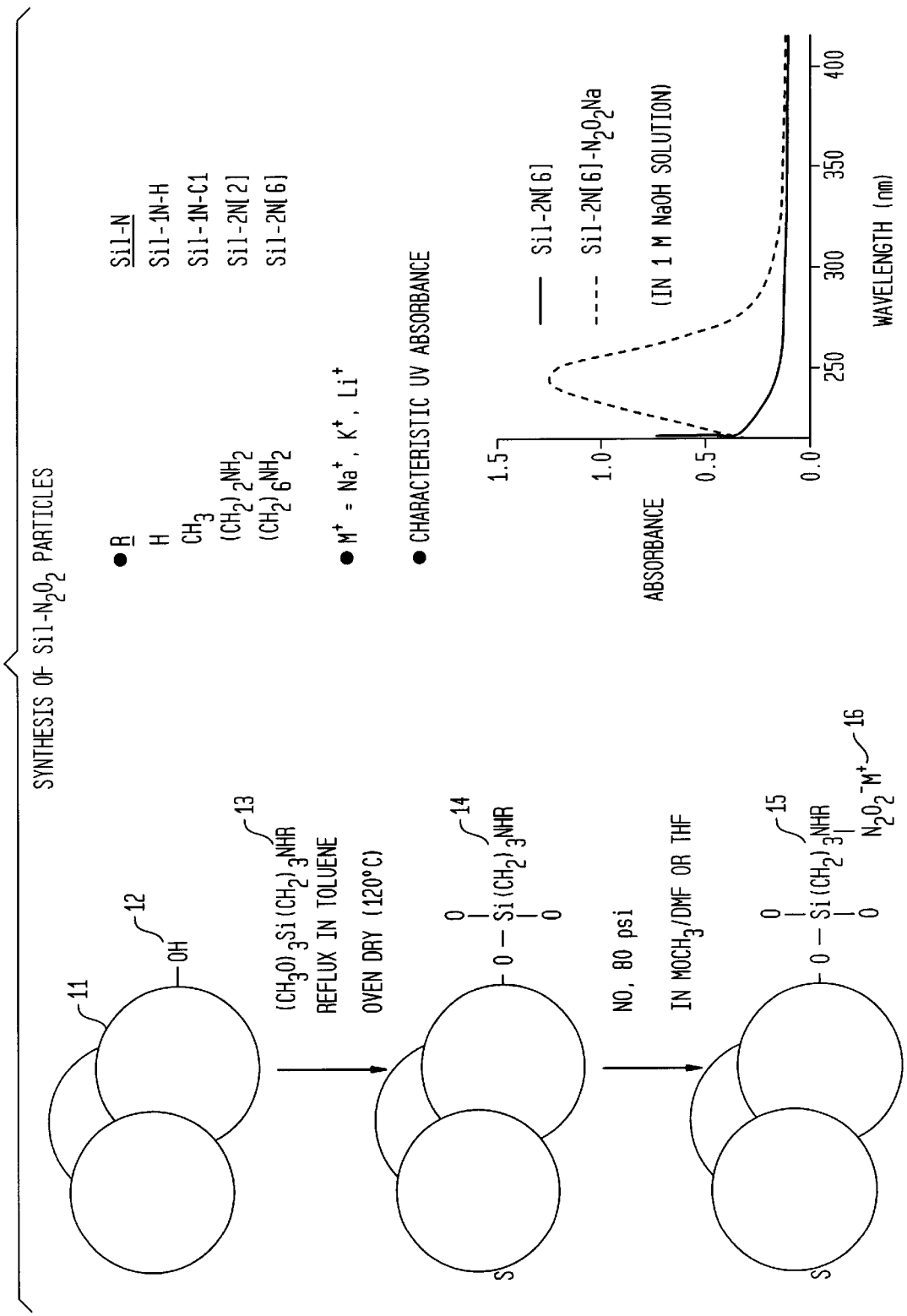

NO-RELEASE IN PBS (pH=7.4) AT 37 °C

CROSS SECTION OF THE PU/Sil-N$_2$O$_2$ COATING ON PVC TUBING

CONTROL CIRCUIT SURFACE

NO-RELEASE CIRCUIT SURFACE

NITRIC OXIDE-RELEASING POLYMERS INCORPORATING DIAZENIUMDIOLATED SILANE DERIVATIVES

RELATIONSHIP TO OTHER APPLICATION(S)

This application is a continuation, and claims the benefit, of U.S. Ser. No. 60/314,177 filed on Aug. 21, 2001.

GOVERNMENT RIGHTS

This invention was made under contract awarded by the National Institutes of Health, Contract Number GM 56991. The government has certain rights in the invention.

BACKGROUND OF THE INVENTION

1. Field of the Invention

This invention relates generally to polymers having improved biocompatibility, and more particularly, to polymers capable of releasing nitric oxide in situ when contacted with blood.

2. Description of the Related Art

Although medical devices, such as extracorporeal circuits and hemodialysis tubes, are widely used in clinical settings, the polymers typically used to fabricate such devices (PVC, polyurethane, silicone rubber, etc.) are still subject to platelet aggregation and adhesion at the polymer-blood contacting surface. Thus, patients are often given anti-clotting agents (i.e., heparin) systemically in order to reduce thrombosis on the surface of these devices. There is, therefore, a need for polymers that more closely simulate the antithrombogenic properties of the endothelial cells that line blood vessels in order to obviate the need to administer anticoagulants.

Nitric oxide (NO) is an important intracellular and intercellular messenger molecule that plays an important physiological role in platelet anti-activation, vascular relaxation, neurotransmission, and immune response. Synthetic materials that release low levels of NO would, therefore, more closely simulate the natural activity of endothelial cells, and therefore, would have improved biocompatibility.

Diazeniumdiolates are known NO release agents. Diazeniumdiolates can be prepared by the reaction of secondary amines with NO at elevated pressure as shown in Eqn. (1) on FIG. 1. In the presence of water, the diazeniumdiolate releases NO and reverts to the secondary amine as shown in Eqn. (2) on FIG. 1. Diazeniumdiolates have been incorporated into polymeric films and used to fabricate intravascular sensors with improved in vivo sensor performance and as internal coatings for tubing in extracorporeal circuits to prevent thrombus formation resulting from prolonged blood contact.

The disclosed approaches taken for preparing NO-releasing polymers include anchoring the diazeniumdiolate to the polymer matrix and anchoring the diazeniumdiolate to fumed silica, of the type already used as a filler in polymers. In one known embodiment, hydroxy-terminated polydimethylsiloxane (or silicone rubber), which is widely used for medical purposes, was crosslinked with a diaminopropyl-trimethoxy silane cross-linking agent, specifically N-(6-aminohexyl)aminopropyl-trimethoxysilane. The cross-linked silicone rubber was then soaked in a solvent, purged with an inert gas, and loaded with NO under pressure.

In another known embodiment, a diaminopropyl-trimethoxy silane was coupled with fumed silica to form diamino-silica. The diamino-silica was charged with NO under pressure to form diazeniumdiolated fumed silica. The diazeniumdiolated fumed silica was then used as a reinforcing filler in silicone rubber films.

In the aforementioned known embodiments, long term release of NO was observed (over at least 10 days), the release rate being higher during the first couple of days and decreasing thereafter. The cross-linked silicone rubber generated only 13% of the theoretical amount of NO, while the fumed silica-filled silicone rubber released only 38% of the theoretical amount.

Experiments conducted in vitro with oxygen-sensing catheters coated with diazeniumdiolate-doped silicone rubber indicate that the diazeniumdiolate and its decomposition products (N,N'-dimethylhexadiamine and the corresponding nitrosamine) have been shown to leach from the polymer films into aqueous soaking solutions. While systemic administration of diazeniumdiolates has been suggested (see, U.S. Pat. No. 5,155,137), it is not clear whether the original species and/or its corresponding decomposition products are safe for human use in this manner. There have been no published reports regarding the specific toxicity of N,N'-dimethyl-N-nitroso-1,6-hexadiamine, for example. However, it has been reported that 90% of the more than 300 nitrosamines that have been tested exhibit carcinogenic properties. Therefore, there is a need for a NO-releasing polymer that does not permit, or at least minimizes, leaching of the diazeniumdiolate and/or its decomposition products, and particularly nitrosamines, into the blood.

Prior art methods of minimizing leaching have included the use of more hydrophobic polymers; the use of linear polyethylenimines rather than branched diamines to form the diazeniumdiolate; the addition of a top coat of un-doped polymer over the diazeniumdiolate donor molecule-doped polymer; and covalent attachment of the diazeniumdiolate group to the polymer backbone. However, leaching can still occur through the polymers having a hydrophilic nature. And, for more hydrophobic embodiments, such as silicone rubber cross-linked with a diazeniumdiolate, other toxic species are generated and released in addition to NO. While anchoring the diazeniumdiolate to silica particles helps control leaching of the diazeniumdiolate and its decomposition products from the polymer, the silica particles are subject to leaching. There is, therefore, a need for polymers having NO-releasing capabilities that do not leach undesired, and potentially toxic, matter into the surrounding aqueous environment.

SUMMARY OF THE INVENTION

The foregoing and other objects are achieved by this invention which provides polymers having improved biocompatibility wherein a NO-releasing diazeniumdiolate group is immobilized to fumed silica, or an inorganic oxide, such as a metal oxide, and is used as a reinforcing filler in a medical grade polymer, such as silicone rubber, poly(vinyl chloride), polyurethane, or the like. In accordance with the present invention, the NO-releasing polymer containing the derivatized fumed silica is included as an inner layer in a multi-layer structure. The term "inner layer" is used to refer to a layer that does not have a blood-contacting surface. One or more top (or base) coats of polymer, which may or may not be of the same general composition as the NO-releasing layer, are included to prevent leaching of the diazeniumdiolate and its decomposition products. One or more of the top or base coats may have a blood-contacting surface. It has been discovered that the top coats are not subject to significantly increased platelet activation or aggregation. Furthermore, the top coats do not interfere with the desirable flux rate of NO at the polymer-blood contacting surface. In addition, the top coats may provide a smoother, exterior blood-contacting surface at the polymer-blood interface.

The NO flux from the surface of endothelial cells (EC) has been estimated by Vaughn, et al., *Am. J. Physiol.*, Vol. 274 (*Heart Circ. Physiol.*, Vol. 43) page H2163 (1998) to be $4.1 \times 10^{-10}$ mole. $cm^{-2}.min^{-1}$. Based on experimental data published by Radomski, et al., *S. Proc. Natl. Acad. Sci. USA*, Vol. 87, page 5193 (1990), it is estimated that the NO flux from bradykinin stimulated EC is about $1.6 \times 10^{-10}$ mole.$cm^{-2}.min^{-1}$ and about $0.50 \times 10^{-10}$ mole.$cm^{-2}.min^{-1}$ for unstimulated EC. These data suggest that a continuous NO flux on the order of $10^{-10}$ mole.$cm^{-2}.min^{-1}$ from the inner surface of blood vessels would successfully inhibit platelet activation and aggregation. Synthetic polymers, with equal or even higher NO fluxes, from their surfaces should be able to effectively prevent platelet adhesion on the polymers. Therefore, the polymer structure of the present invention is fabricated to produce an NO flux rate at its surface that is greater than, or equal to, the estimated flux rate of NO from the endothelial cells that line the walls of all blood vessels.

In preferred embodiments, the multilayered polymers of the present invention yield surface NO fluxes on the order of $10^{-10}$ mole.$cm^{-2}.min^{-1}$ for more than 24 hours. This simulates the normal fluxes of NO that arise from the layer of endothelial cells lining the walls of blood vessels and provides a thromboresistant surface for use in a variety of biomedical applications.

More specifically, amino silanes, and preferably di-or tri-amino silanes, are used to derivatize fumed silica particles. Amine functionalities on the derivatized fumed silica particles are loaded with NO under pressure to form diazeniumdiolates. The loaded, derivatized fumed silica particles may then be dispersed into any desired polymer. Upon contact with blood (water), the diazeniumdiolates decompose to NO and the corresponding amine.

As used herein, the amino silane coupling agents include, without limitation, mono-, di-, and tri-amino silanes. Preferably, di- and/or tri-amino silanes, or mono-, di-, or tri-amino silanes containing one secondary amine, are used because they can be loaded with greater amounts of NO. In the specific illustrative embodiments presented herein, the preferred amino silane coupling agents are N-(2-aminoethyl)-aminopropyl-trimethoxysilane and N-(6-aminohexyl)aminopropyl-trimethoxysilane. Other agents include, without limitation, N-methylaminopropyl-trimethoxysilane and 3-trimethoxysilylpropyl)-diethylenetriamine. All of these agents are available commercially from Gelest, Tullytown, Pa.

Fumed silica is a term used for amorphous silicon dioxide particles, having reactive silanol and siloxane moieties at the surface, commonly used as a filler in polymer formulations for reinforcement and/or rheology control. In the specific illustrative embodiments herein, the fumed silica was Cab-O-Sil brand untreated filmed silica available from Cabot, Tuscola, Ill., having primary particle sizes ranging from 7–27 nm with aggregates in the range of from 0.2–0.3 micrometers and surface areas of 380–100 $m^2/g$. In this specific embodiment, there are about 2.5 to 4.5 silanol groups/$nm^2$ on the surface. However, it is to be understood that fumed silica is available commercially from many sources and that other brands of fumed silica, particularly those having high surface areas, would be suitable for the practice of the invention.

In addition to fumed silica, other inorganic oxides, and specifically metal oxides, such as platinum oxide, titanium dioxide, or tin oxide, can be derivatized and loaded with NO under pressure to form NO-releasing diazeniumdiolates.

Polymers suitable for the practice of the invention include, but are not limited to, any typically used medical-grade, and preferably non-biodegradable, polymers, such as silicone rubber, poly(vinyl chloride), polyurethane, polycaprolactone, etc. It is also to be understood that the term polymer is to be construed to include copolymers and oligomers. Hydrophobic polymers are preferred, and in some embodiments, the polymers can be plasticized.

Plasticizers are optional, and in fact, typically are not required in silicone rubber formulations. In polyurethane or PVC formulations, for example, plasticizers may be added, as is known in the art, to achieve the desired flexibility. Plasticizers also facilitate the uptake of water, and hence, would be expected to facilitate NO release from the polymer. Illustrative plasticizers that have been used in the practice of the invention include, without limitation, 2-nitro octyl ether (NPOE) and dioctyl sebacate (DOS). However, other plasticizers are suitable for preparing NO-releasing polymeric films in accordance with the present invention. Such additional plasticizers include, without limitation, isopropyl palmitate, isopropyl isostearate, diisooctyl phthalate, as well as many others known in the art.

It is to be understood, however, that the terms "polymer" or "biocompatible polymer" denote any synthetic or naturally-derived polymeric material which is known, or becomes known. Biocompatible polymers are particularly suited for in-dwelling uses in the body of a living being, i.e., are biologically inert and physiologically acceptable, and are non-toxic. In the preferred embodiments of the present invention, the polymer is synthetic, biocompatible, and non-biodegradable. Illustrative examples further include polydimethylsiloxane, ethylene vinyl acetate, polymethyl methacrylate, polyamide, polycarbonate, polyester, polyethylene, polypropylene, polystyrene, polytetrafluoroethylene, and cellulose acetate.

However, the principles of the invention are applicable to polymers that are biodegradable or bioerodable in the environment of use, i.e., can be resorbed by the body, provided that they erode slow enough for the NO-releasing capability to be beneficial. Illustrative examples include, but are not limited to, polyesters, such as polylactides, polyglycolides, and polylactic polyglycolic copolymers (PLGA); polyethers, as such as hydroxy-terminated poly (ε-caprolactone)-polyether or polycaprolactone (PCL); polyanhydrides; polyalkylcyanoacrylates, such as n-butyl cyanoacrylate; polyacrylamides; poly(orthoesters); polyphosphazenes; polyamino acids; and biodegradable polyurethanes.

In typical embodiments, the components of the NO-releasing polymer range from about 30–95% by weight of the basic polymer (e.g., polyurethane or poly(vinyl chloride)); from 0 to about 60% by weight plasticizer (e g., NPOE or DOS); and from about 5–40% by weight diazeniumdiolated fumed silica.

In a specific illustrative method of making embodiment of the invention, fumed silica is refluxed in a solvent, illustratively toluene, in the presence of a diamino coupling agent to form the diaminated silica (SilN). The diaminated silica is loaded with NO under pressure, preferably with a methoxide base for reasons that will be discussed hereinbelow, to form the diazeniumdiolated fumed silica ($SilN_2O_2$). $SilN_2O_2$ is then dispersed in a solution of the desired polymer to form a NO-releasing polymer. However, it is a significant advantage that $SilN_2O_2$ can be stored in powdered form and incorporated into a polymer at a later time. Moreover, since the $SilN_2O_2$ is charged with NO prior to incorporation into the desired polymer, there is no need to charge an entire device that has been already cast, molded, or otherwise formed from a diazeniumdiolated polymer, with NO.

A multilayer structure is formed by alternately casting from a solvent, dip-coating, or otherwise forming, a layer of NO-releasing polymer and a layer of plain (un-doped) polymer. In preferred embodiments of the present invention, the NO-releasing polymer layer comprises at least one of an inner layer in a multi-layer structure. The multilayer structure includes one or more top (or base) coats of a polymer, which may or may not be of the same basic polymer as in the NO-releasing polymer layer. A base, or bottom, coat is particularly preferred in embodiments where the type of polymer in the surface adjacent to the NO-releasing polymer is of different composition. In this case, a base coat can assist adhesion between the layers. The multilayer structure constrains leaching of the silica particles from the NO-releasing layer into the surrounding aqueous environment.

BRIEF DESCRIPTION OF THE DRAWING

Comprehension of the invention is facilitated by reading the following detailed description, in conjunction with the annexed drawing, in which:

FIG. 2 is an illustrative synthetic route for forming derivatized fumed silica particles;

FIG. 2A is a graphical representation of the characteristic UV absorbance of an aminated-silica and a diazeniumdiolated silica as a function of wavelength in nm;

DETAILED DESCRIPTION

Figure 1:
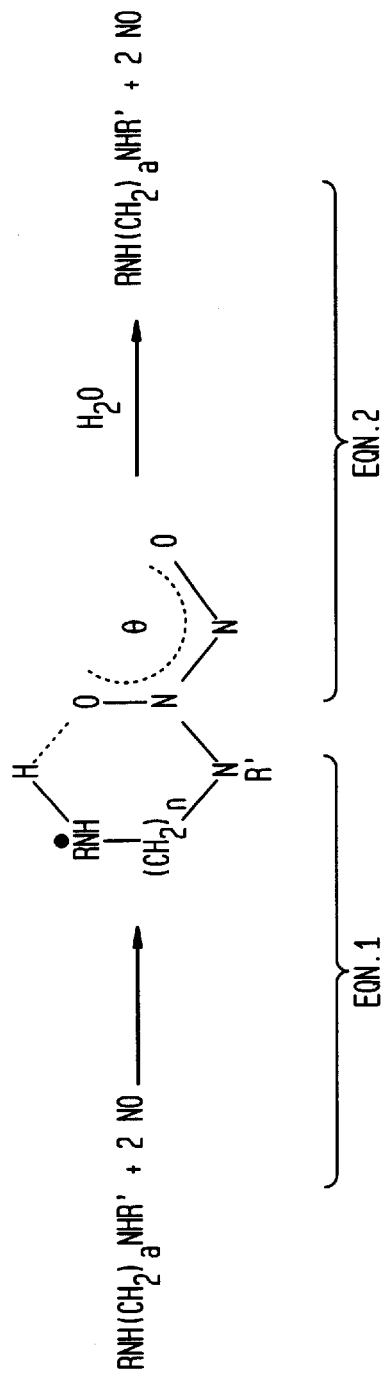
FIG. 1 shows the chemical reaction pathway between a secondary amine $(RNH(CH_2)_n)NHR')$ and nitric oxide to a diazeniumdiolate (Eqn. 1) and the subsequent decomposition of the diazeniumdiolate into the amine and NO (Eqn. 2) upon contact with water.

In an illustrative method of making embodiment of the invention, as shown in FIG. 2, fumed silica 11(Cab-O-Sil EH-5, surface area 380 m$^2$/g, Cabot, Tuscola, Ill.) was suspended in toluene and refluxed under stirring. Fumed silica has reactive silanol groups 12 on its surface. In this specific embodiment, there are about 2.5 to 4.5 silanol groups/nm$^2$ on the surface.

An equivalent amount of an amino silane coupling agent 13 in toluene was added to the fumed silica suspension. The mixture was further refluxed and stirred overnight to produce derivatized fumed silica 14. In this particular embodiment, the amino silane coupling agent 13 has the formula: $(CH_3O)_3Si(CH_2)_3)NHR$ where R may be H, $CH_3$, $(CH_2)_2NH_2$, and $(CH_2)_6NH_2$. Of course, in the embodiment where R is H, the amino silane is a primary amine. As will be seen from the discussion hereinbelow, particularly preferred coupling agents are the latter three, or N-methylaminopropyl-trimethoxysilane, N-(2-aminoethyl)-aminopropyl-trimethoxysilane and N-(6-aminohexyl)aminopropyl-trimethoxysilane. All of these agents are available commercially from Gelest, Tullytown, Pa.

The derivatized fumed silica 14 was centrifuged at 3000 rpm, rinsed with toluene three times, and then oven-dried at about 120° C. overnight. CHN elemental analysis indicated that about 50–80% of the amino silane was coupled onto fumed silica (Sil) to form the derivatized fumed silica, or aminated-silica (SilN) 14. The composition of the resulting aminated-silica compound, of course, depends on the composition of the amino silane coupling agent. For the specific illustrative amino silane coupling agents covered by the formula $(CH_3O)_3Si(CH_2)_3)NHR$, where R is as indicated, the aminated-silica compounds are designated herein by the following nomenclature:

| R | Sil—N |
|---|---|
| H | Sil—1N—H |
| $CH_3$ | Sil—1N—Cl |
| $(CH_2)_2NH_2$ | Sil—2N[2] |
| $(CH_2)_6NH_2$ | Sil—2N[6] |

The aminated-silica 14 was dispersed in a solvent, illustratively 10% 0.2N sodium methoxide/methanol in N,N'-dimethylformamide (DMF) or tetrahydrofuran (THF) (dried over 4 Å molecular sieves), purged with Argon, and charged with NO to 80 psi under stirring for 10–168 hours, preferably about 24 hours, to obtain diazeniumdiolated fumed silica $(SilN_2O_2)$ 15. A chemiluminescence NO analyzer, CHN elemental analysis, and the photometric Greiss assay (see, Schmidt, et al., In *Methods of Nitric Oxide Research*, Feelisch, et al., eds., page 41ff, John Wiley, New York, (1996)) indicated that 20–50% of the amino groups were diazeniumdiolated. A typical NO loading for $SilN_2O_2$ is about 600 μmol/g. When dissolved in a 1 N NaOH solution, $SilN_2O_2$ shows the characteristic diazeniumdiolate absorbance band with a maximum absorbance at 246 nm for secondary amines and 252 nm for primary amines. This band disappears when the $SilN_2O_2$ is decomposed by water. Referring to FIG. 2A, the characteristic UV absorbance of the aminated-silica Sil-2N[6] and the diazeniumdiolated fumed silica Sil-2N[6]-$N_2O_2$Na, in a 1M NaOH solution, are shown as a function of wavelength in nm.

Studies were conducted that demonstrated that NO loading of fumed silica derivatized with N-(6-aminohexyl) aminopropyl-trimethoxysilane was affected by the solution in which the particles were dispersed during NO charging. Low loading was achieved in plain organic solvents (0.2–2.0 mmol/g NO) or medium bases (0.1–0.2 mmol/g NO), such as sodium acetoxide or sodium phenoxide, whereas high loading was achieved with strong bases, such as sodium methoxide or sodium trimethylsiloxide.

In addition to the foregoing, studies were conducted to ascertain whether the counterion in the diazeniumdiolate zwitterion affected NO loading and/or decomposition. To vary the counter cations ($M^+$), sodium methoxide, potassium methoxide and lithium methoxide were used as the solvent during NO charging. Tables 1 and 2 below demonstrate that the counter cations $Na^+$, $K^+$, or $Li^+$ have minimal effect on the formation of the diazeniumdiolate in terms of NO loading as measured using a chemiluminescence NO analyzer to measure NO using the chemiluminescence reaction between NO and ozone (Table 1), or by measuring the molar absorptivity at 246 nm for secondary amines or 252 nm for primary amines ($\epsilon_{max}$, $mM^{-1}.cm^{-1}$) (Table 2).

TABLE 1

NO Loading of Derivatized Fumed Silica (mmol/g)

| SilN | $Na^+$ | $K^+$ | $Li^+$ |
|---|---|---|---|
| Sil—2N[6] | 0.57 | 0.60 | 0.61 |
| Sil—2N[2] | 0.58 | 0.36 | 0.65 |
| Sil—1N—Cl | 0.58 | 0.35 | 0.60 |
| Sil—1N—H | 0.08 | 0.06 | 0.01 |

TABLE 2

Molar Absorptivity of Diazeniumdiolate at $\epsilon_{max}$ ($mM^{-1} \cdot cm^{-1}$)

| SilN | $Na^+$ | $K^+$ | $Li^+$ |
|---|---|---|---|
| Sil—2N[6] | 12.6 | 12.8 | 13.8 |
| Sil—2N[2] | 13.1 | 13.5 | 11.8 |
| Sil—1N—Cl | 11.1 | 11.6 | 10.3 |
| Sil—1N—H | 39 | 47 | 46 |

Furthermore, the counter cation had minimal effect on the rate of diazeniumdiolate dissociation as shown in Table 3. The half-life ($t_{1/2}$, min.) of the diazeniumdiolates in phosphate-buffered saline (PBS, pH=7.4) at 37° C. was measured with a chemiluminescence NO analyzer. As is known, the release rate of NO from a given diazeniumdiolate, incorporated into a polymer, is proportional to the half-life of its release rate in buffer.

TABLE 3

Half-Life ($t_{1/2}$, min.) of the Diazeniumdiolates in PBS (pH = 7.4) at 37° C.

| SilN | $Na^+$ | $K^+$ | $Li^+$ |
|---|---|---|---|
| Sil—2N[6] | 42 ± 3 | 40 | 37 |
| Sil—2N[2] | 144 ± 2 | 118 | 170 |
| Sil—1N—Cl | 5.2 | 6.8 | 7.2 |
| Sil—1N—H | 56 | 53 | 26 |

Advantageously, derivatized fumed silica particles can be pre-loaded with NO and used at a later time in any desired polymer. The $SilN_2O_2$ particles are relatively stable when stored at freezing temperatures, but slowly decompose at room temperature. Tables 4 and 5 shows the half-life of $SilN_2O_2Na$ particles at various pH and temperatures.

TABLE 4

For Sil—2N[6]—$N_2O_2$Na particles:

| pH | 6 | 7.4 | 9 | 11 |
|---|---|---|---|---|
| $t_{1/2}$ (min) | 13.2 ± 0.2 | 42 ± 3 | 112 | ≧4000 |

TABLE 5

$t_{1/2}$ (min) of Sil—2N[6]—$N_2O_2$M particles at different temperatures

| $M^+$ | −15° C. | 0° C. | 23° C. | 80° C. |
|---|---|---|---|---|
| $Na^+$ | ≧1.2 × $10^5$ | ≧1.3 × $10^4$ | ≧1.5 × $10^3$ | 23 |
| $K^+$ | ≧1.7 × $10^5$ | 3.0 × $10^4$ | ≧3.0 × $10^3$ | 30 |
| $Li^+$ | ≧0.9 × $10^5$ | ≧2.1 × $10^4$ | N/A | 130 |

The diazeniumdiolate derivatized fumed silica ($SilN_2O_2$) is incorporated into a polymer by dispersing between 5–40 wt %, and preferably between about 10–20 wt %, in a solution of the polymer and then solvent casting or dip-coating to form thin films of NO-releasing polymer on a surface. In one specific illustrative embodiment, polyurethane (medical grade Carbothane PC 357A (135 mg) was dissolved in THF (1 ml). A fine dispersion of $SilN_2O_2$ (15 mg) in THF (1 ml) was obtained by sonication, added to the polymer solution, and vortexed. The mixture was cast on a Teflon plate/glass well and cured in air overnight.

In another specific illustrative embodiment, low molecular weight PVC (Fluka, 9 mg) was dissolved in THF (1 ml). A fine dispersion of $SilN_2O_2$ (15 mg) in THF (1 ml) was obtained by sonication for 10 minutes, added to the polymer, and vortexed. The mixture was cast on a Teflon plate and cured in air overnight.

In yet another illustrative example, diazeniumdiolated fumed silica was used as a reinforcing filler to prepare silicone rubber polymer films using the following technique: hydroxy-terminated polydimethylsiloxane (viscosity 20,000 cSt, 320 mg), methyl-trimethoxysilane (10.2 mg), and dibutyltin dilaurate (6.4 mg) were dissolved in toluene (1.9 ml). A fine dispersion of diazeniumdiolated fumed silica (18 mg) in toluene (1 ml) was added to the polymer solution, vortexed, and sonicated for 10 minutes. The mixture was cast on a Teflon plate and cured in air for 2 days to form a diazeniumdiolated fumed silica silicone rubber film.

Figure 3:
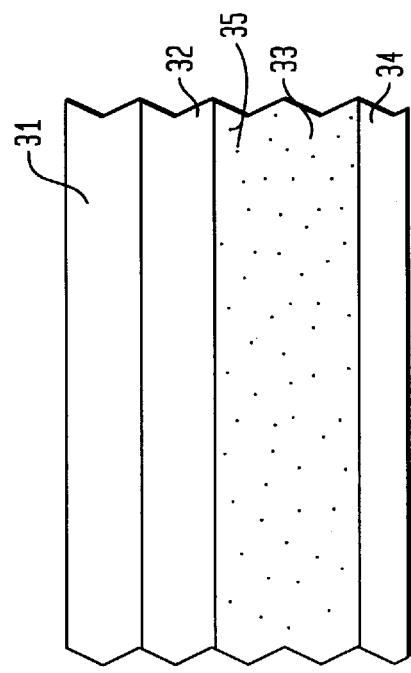
FIG. 3 is a schematic representation of a multilayer polymer in accordance with the present invention.

NO-releasing polymers of the type disclosed hereinabove are then incorporated as an inner layer in a multilayer structure of the type shown schematically in FIG. 3. Referring to FIG. 3, NO-releasing polymer layer 33, having the diazeniumdiolated fumed silica (e.g., particles 35) dispersed therein, is sandwiched between at least one polymer top coat 32 and a bottom substrate 34. In the embodiment shown, there are two polymeric top coats 32 and 31, coat 31 having the blood-contacting surface 36. Layers 32 and 31 are plain base polymers and do not contain diazeniumdiolated fumed silica. However, the top coats do not interfere with the desirable flux rate of NO at the polymer-blood contacting surface. The bottom substrate 34 may be another layer of plain polymer or it may be a surface of another device, such as PVC tubing of the type used in extracorporeal circuits or a metallic stent or electrode lead. For an actual image of a multilayer structure of the type shown in FIG. 3, see FIG. 7 which is a scanning electron micrograph of coated PVC tubing.

Of course, the multilayer structure of FIG. 3 is purely illustrative, and it is to be understood than many alternate embodiments can be devised within the spirit and scope of the invention. For example, the multilayer structure can incorporate more than one interior layer of a NO-releasing polymer.

The following specific examples were fabricated with diazeniumdiolated fumed silica and used in the experiments reported hereinbelow:

Film #1 (Prior Art)

Polyurethane monolayer films, about 16 mg per disc (1 cm), were formed by solvent casting to have the following compositions by weight percent: 45% polyurethane; 45% 2-nitrophenyl octyl ether (NPOE; Fluka, Switzerland); and 10% loading with diazeniumdiolated fumed silica (specifically, Sil-2N[6]$N_2O_2$Na, as shown on FIG. 2).

Film #2 (Prior Art)

A second polyurethane film having twice the Sil$N_2O_2$ loading was formed to have the following composition by weight percent: 40% polyurethane; 40% NPOE; and 20% loading with Sil-2N[6]-$N_2O_2$Na.

Film #3

In this specific illustrative embodiment, a tri-layer structure was formed to have the overall composition 30% polyurethane; 60% NPOE; and 10% Sil$N_2O_2$ in a multilayer structure where the top and bottom layers were plasticized polyurethane (1:2 by wt PU/NPOE) and the middle layer was 1:2:1 by wt PU/NPOE/Sil-2N[6]$N_2O_2$Na.

Film #4

A multilayer coating was formed on the inner wall surface of ¼" PVC tubing. The four layer structure comprised: a polyurethane bottom coat adjacent the tubing surface; a polyurethane/Sil$N_2O_2$ layer, a polyurethane top coat on the NO-releasing layer, and a second top coat of PVC as the blood-contacting surface. The total thickness of this multilayer coating was about 250 micrometers.

Experimental Data

NO Release Studies

Films #1–#3 were cut into 1 cm diameter disks and soaked in 5 ml aliquots of phosphate buffered saline (PBS; pH 7.4; Sigma, St. Louis, Mo.) placed in a shaker incubator at 37° C. NO levels in the PBS were determined indirectly by measuring nitrite levels using the Greiss assay.

Figure 4:
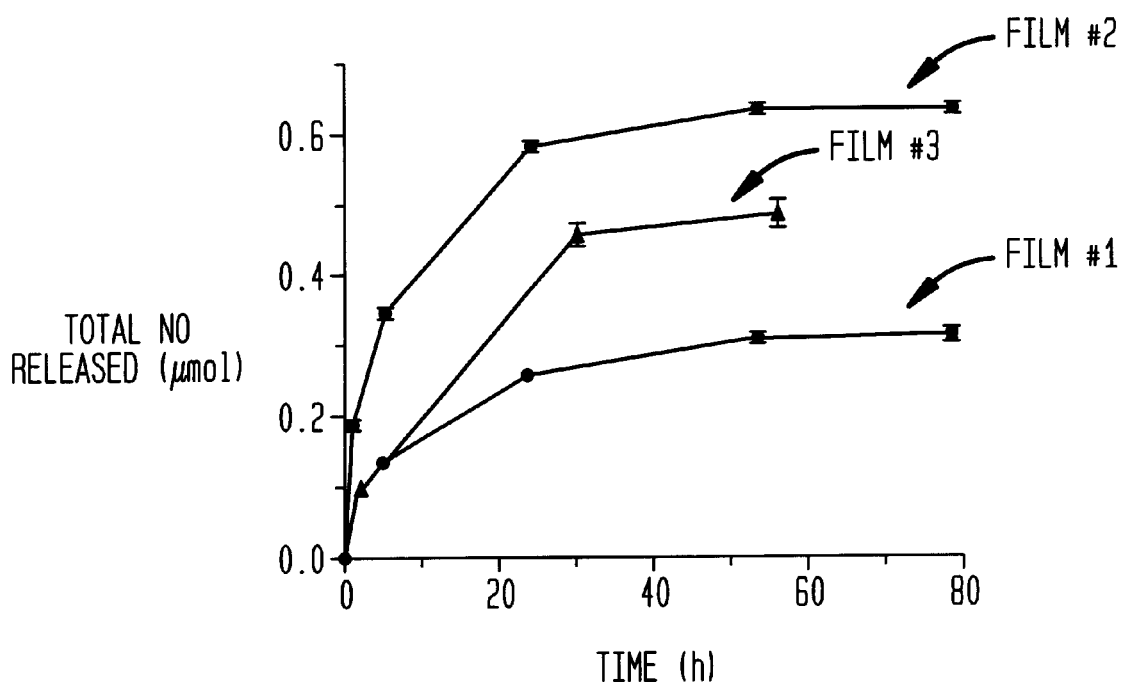
FIG. 4 is a graphical representation of the NO release profiles for polyurethane films incorporating $SilN_2O_2$.

The results are shown on FIG. 4, which is a graphical representation of the NO release profiles of the polymer films, shown as the total NO released (measured in $\mu$mol) as a function of time in hours.

Although most Sil$N_2O_2$ particles have a half-life of within an hour in PBS buffer at 37° C., they release NO for a prolonged period of time when incorporated into a polymer matrix. As shown in FIG. 4, polyurethane films having varying Sil$N_2O_2$ loading, bathed in PBS at 37° C., continuously emit NO over a three day period. The amount of NO generated was nearly proportional to the Sil$N_2O_2$ loading for similar film compositions.

In film #3, Sil$N_2O_2$ was only incorporated into the middle layer of a tri-layer film in order to minimize leaching of Sil$N_2O_2$. Surprisingly, the tri-layer configuration exhibited a slightly faster NO generation rate than the monolayer compositions (Films #1) with the same Sil$N_2O_2$ loading. However, this particular tri-layer film (Film #3) contained 15% more plasticizer than the monolayer film (Film #1). Higher plasticizer content may result in a faster water uptake rate and, thus, higher NO flux, from the Sil$N_2O_2$-loaded films.

Figure 5:
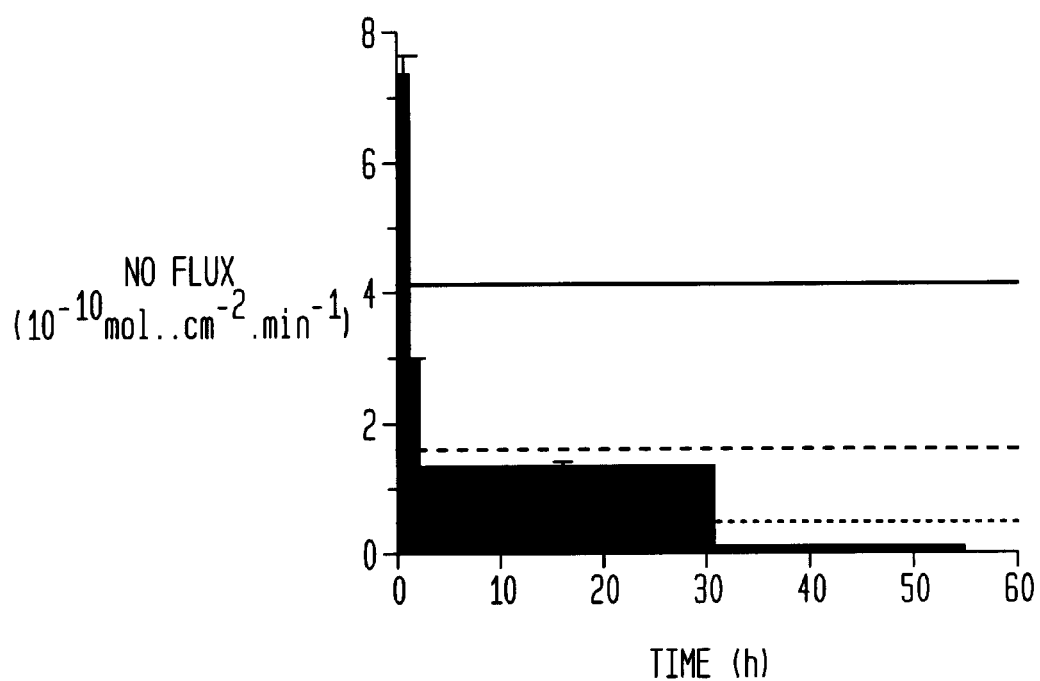
FIG. 5 is a graphical representation of the mean NO flux $(10^{-10}$ mole.cm$^{-2}$.min$^{-1})$ over time in hours for a tri-layer structure in accordance with the invention.

FIG. 5 is a graphical representation of the mean NO flux ($10^{-10}$ mole.cm$^{-2}$.min$^{-1}$) over time in hours for the tri-layer structure (Film #3). The solid line indicates the NO production rate from endothelial cells as estimated by Vaughn, et al., *Am. J. Physiol.*, Vol. 274 (*Heart Circ. Physiol.*, Vol. 43) page H2163 (1998). The dashed and dotted lines indicate the NO flux from bradykinin stimulated and unstimulated endothelial cells, respectively, as estimated based on data published by Radomski, et al, *S. Proc. Natl. Acad. Sci. USA*, Vol. 87, page 5193 (1990).

As shown in FIG. 5, the NO fluxes from the Sil$N_2O_2$-loaded polyurethane film #3 were comparable to those produced by endothelial cells up to 30 hours, and were very high during the first two hours. This film is expected to have good blood compatibility since the observed levels of NO fluxes should effectively prevent platelet activation and aggregation on the film's surfaces.

Figure 6:
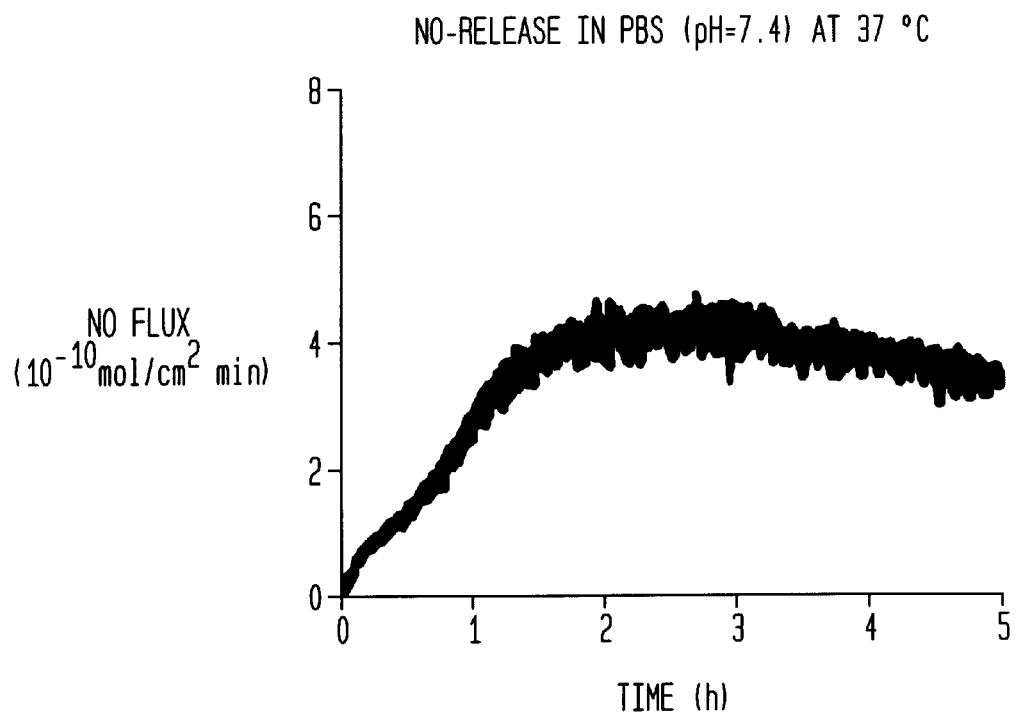
FIG. 6 is a graphical representation of the mean NO flux $(10^{-10}$ mole.cm$^{-2}$min$^{-1})$ over time in hours for a multilayer structure in accordance with the invention.
Figure 7:
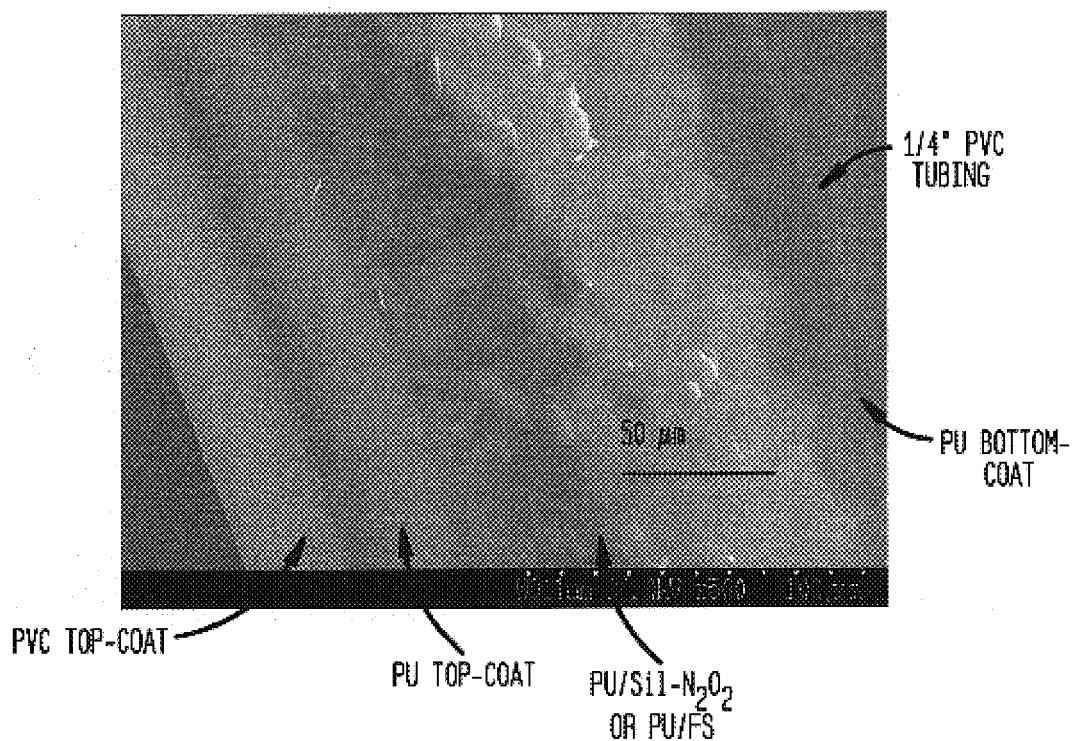
FIG. 7 is a scanning electron micrograph image of a cross-section of a PVC tube coated with a NO-releasing multilayer film in accordance with the invention.

FIG. 6 is a graphical representation of the NO flux from the multilayered film #4 on PVC tubing in phosphate buffered saline at pH 7.4 at 37° C. The NO flux, at about $4\times10^{-10}$ mole.cm$^{-2}$.min$^{-1}$ is comparable to that produced by the endothelial cells. FIG. 7 is a scanning electron micrograph image of a cross-section of the multilayer-coated PVC tubing (Film #4) used in this experiment. Referring to FIG. 7, a polyurethane bottom coat is seen adjacent the inner surface of ¼" PVC tubing, followed by the NO-releasing layer of polyurethane with diazeniumdiolated fumed silica. A polyurethane top coat is adjacent to the NO-releasing layer followed by a second top coat of PVC.

An in vivo experiment was conducted using the multilayer-coated PVC tubing (Film #4) in an extracorporeal circuit. The tubing was connected to rabbits through cannulas for venovenous circulation via a roller pump. Blood was circulated through the tubing for 4 hours at a rate of about 100 ml/min.

Figure 8:
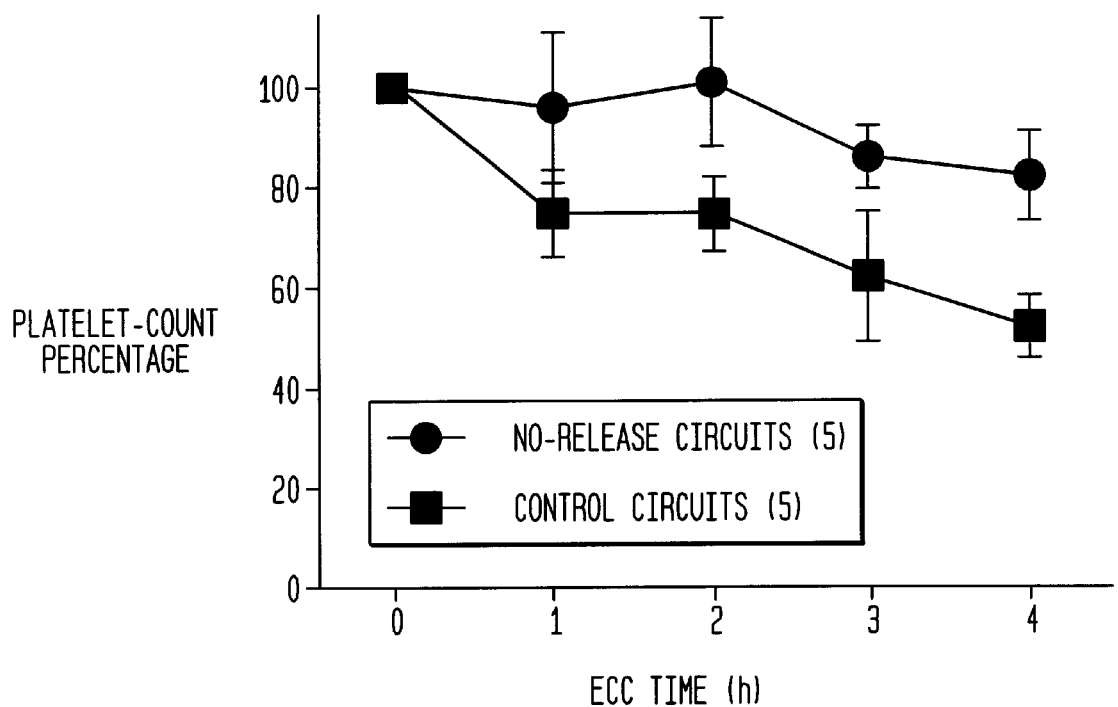
FIG. 8 is a graphical representation of blood platelet count expressed as a percentage of initial, or baseline, platelet count versus time in hours for an in vivo experiment conducted with a multilayer embodiment of the present invention.

FIG. 8 is a graphical representation of the platelet count expressed as a percentage of initial platelet count versus time in hours. In a study of ten rabbits, 5 with the NO-releasing PVC tubing in the circulation circuit and 5 with plain PVC tubing as controls, there was less platelet-count drop observed for the NO-releasing tubing as compared to the control over the 4 hours of circulation.

Figure 9:
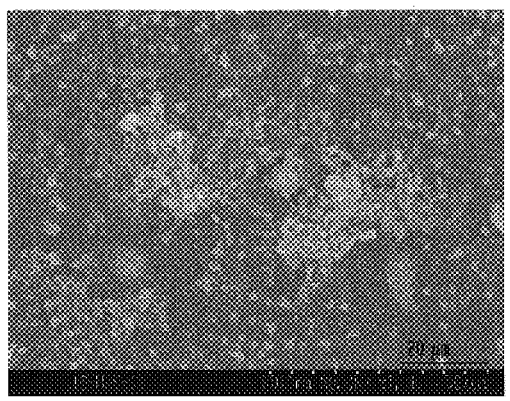
FIGS. 9 and 10 are scanning electron micrograph images made from a cross-section of PVC tubing (control) and NO-releasing tubing, respectively, used in the in vivo experiment.
Figure 10:
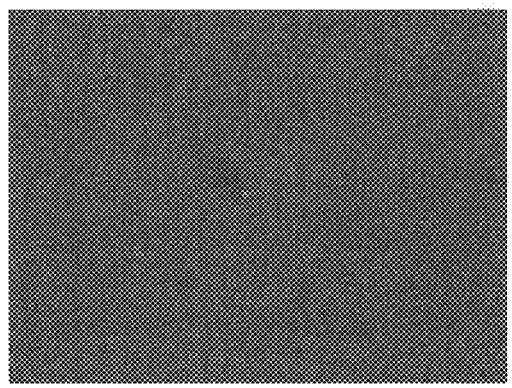

Scanning electron micrograph images were made from a cross-section of the PVC tubing (control) and NO-releasing PVC tubing used in the extracorporeal circulation experiments. The results are shown FIGS. 9 and 10, respectively. FIG. 10 shows much less clotting on the surface of NO-releasing tubing indicating improved thromboresistance.

As is evident from the data presented herein, NO-releasing fumed silica is a good source of NO that may be readily incorporated into different polymer matrices to fabricate multilayer biomaterials having improved blood compatibility. Such biomaterials could be used in a variety of biomedical applications, specifically including, but not limited to, the fabrication of extracorporeal devices and intravascular sensors.

Illustratively, the NO-releasing biocompatible polymer coatings disclosed herein may be used on the blood-contacting surfaces of existing medical or diagnostic devices, such as in-dwelling catheters, plastic extracorporeal tubing sets (including kidney dialysis, open-heart surgery heart-lung machines), and the like. It is to be understood that the NO-releasing polymer coatings of the present invention may comprise a membrane, film, matrix, tubing, or any other device that is likely to come into contact with tissue or blood. Of course, the NO-releasing polymer itself may be cast, molded, or otherwise formed into any desired configuration and subsequently coated with one or more top coats.

Of course, the novel polymers would be useful for fabricating chemical sensors that can continuously monitor or measure physiologically important ions (e.g. $H^+$, $K^+$, $Na^+$) and gases ($CO_2$ and $O_2$) in the blood for intraarterial or extracorporeal applications.

In addition to the foregoing, nitric oxide releasing polymers may also be able to inhibit bacterial adhesion and growth on the surface of in-dwelling polymeric devices, such as urinary catheters. Therefore, the term "blood-contacting surface" can refer to any liquid, or body fluid, contacting surface.

Although the invention has been described in terms of specific embodiments and applications, persons skilled in the art can, in light of this teaching, generate additional embodiments without exceeding the scope or departing from the spirit of the invention described herein. Accordingly it is to be understood that the drawing and description in this disclosure are proffered to facilitate comprehension of the invention, and should not be construed to limit the scope thereof.

What is claimed is:

1. A thromboresistant device that releases NO at a blood-contacting surface thereof, said device comprising:
    a NO-releasing layer of a polymer having dispersed therein derivatized fumed silica that has a NO-releasing diazeniumdiolate group immobilized on the silica surface; and
    a coating of a biocompatible polymer on the NO-releasing layer, the coating providing the blood-contacting surface.

2. The device of claim 1 wherein there is provided at least a second coating of a polymer.

3. The device of claim 1 wherein the polymer is a medical-grade, non-biodegradable, polymer.

4. The device of claim 3 wherein the polymer is a hydrophobic polymer.

5. The device of claim 3 wherein the medical grade polymer is selected from the group of silicone rubber, poly(vinyl chloride), polyurethane, and polycaprolactone and copolymers thereof.

6. The device of claim 3 wherein the polymer in the NO-releasing layer further includes a plasticizer.

7. The device of claim 6 wherein the plasticizer is selected from the group consisting of 2-nitro octyl ether, dioctyl sebacate, isopropyl palmitate, isopropyl isostearate, and diisooctyl phthalate.

8. The device of claim 1 wherein the blood-contacting surface has an NO flux rate that is greater than, or equal to, the flux rate of NO from the endothelial cells that line the walls of all blood vessels.

9. The device of claim 8 wherein the NO flux ate is on the order of $10^{-10}$ mole.cm$^{-2}$.min$^{-1}$.

10. The dance of claim 1 wherein the NO-releasing layer comprises:
    about 30–95% by weight of a polymer;
    0 to about 60% by weight plasticizer; and
    from about 5–40% by weight of diazeniumdiolated fumed silica.

11. The device of claim 10 wherein the diazeniumdiolated fumed silica comprises about 10–20% by weight.

* * * * *